United States Patent
Zhang et al.

(10) Patent No.: US 8,020,991 B2
(45) Date of Patent: Sep. 20, 2011

(54) TWO-EYE ADAPTIVE OPTICAL VISUAL PERCEPTION TRAINING METHOD AND APPARATUS THEREOF

(75) Inventors: Yudong Zhang, Sichuan (CN); Yifeng Zhou, Anhui (CN); Yun Dai, Sichuan (CN); Xuejun Rao, Sichuan (CN); Haoxin Zhao, Sichuan (CN)

(73) Assignees: The Institute of Optics and Electronics, The Chinese Academy of Sciences, Chengdu, Sichaun (CN); University of Science and Technology of China, Hefei, Anhui (CN)

( * ) Notice: Subject to any disclaimer, the term of this patent is extended or adjusted under 35 U.S.C. 154(b) by 24 days.

(21) Appl. No.: 12/794,473

(22) Filed: Jun. 4, 2010

(65) Prior Publication Data

US 2011/0149237 A1 Jun. 23, 2011

(30) Foreign Application Priority Data

Dec. 18, 2009 (CN) .......................... 2009 1 0262471

(51) Int. Cl.
*A61B 3/00* (2006.01)
*A61B 3/14* (2006.01)
*A61B 3/10* (2006.01)
(52) U.S. Cl. .......................... 351/203; 351/210; 351/221
(58) Field of Classification Search .................. 351/200, 351/203, 205, 210–212, 221
See application file for complete search history.

(56) References Cited

U.S. PATENT DOCUMENTS

| | | | |
|---|---|---|---|
| 2003/0147048 A1* | 8/2003 | Mihashi | 351/211 |
| 2008/0284979 A1* | 11/2008 | Yee et al. | 351/209 |
| 2008/0297533 A1* | 12/2008 | Kaercher | 345/600 |
| 2010/0073469 A1* | 3/2010 | Fateh | 348/62 |

OTHER PUBLICATIONS

Williams, David R., et al., "Formation and Acquisition of the Retinal Image"; In: J.S.W. Leo M. Chalupa (Ed.) The Visual Neurosciences, The MIT Press, Cambridge, Massachusetts, London, England (2003); pp. 795-810.

(Continued)

*Primary Examiner* — Dawayne A Pinkney
(74) *Attorney, Agent, or Firm* — Osha • Liang LLP

(57) ABSTRACT

The present invention proposes a two-eye adaptive optical visual perception training apparatus, comprising: left and right eye wave aberration measurement sub-systems for measuring eye wave aberrations of the left and right eyes of a person to be tested; left and right eye wave aberration correction sub-systems for driving and controlling the wavefront corrector to correct the wave aberrations of the left and right eyes of the person to be tested based on the measured wave aberrations of the left and right eyes of the tested person; and a two-eye visual perception training sub-system for processing and displaying sighting targets of different spatial frequencies and different contrasts and presenting the sighting targets to the tested person, to conduct a two-eye visual function measurement process and a visual perception training process. By means of the apparatus according to the present invention, finer visual stimulus is obtained by correcting aberrations of two eyes, and then eye acuity limit of the two eyes can be measured, and the visual perception training effect and visual function of the two eyes can be efficiently improved by performing visual perception training on the two eyes with such apparatus.

12 Claims, 2 Drawing Sheets

OTHER PUBLICATIONS

Yoon, Geun-Young, et al., "Visual performance after correcting the monochromatic and chromatic aberrations of the eye"; J. Opt. Soc. Am. A/vol. 19, No. 2 (Feb. 2002); pp. 266-275.

Chiu, Chiayu, et al., "The Role of Neural Activity in the Development of Orientation Selectivity"; J.S.W. Leo M. Chalupa (Ed.) The Visual Neurosciences, The MIT Press, Cambridge, Massachusetts, London, England (2003); pp. 117-125.

Zhou, Yifeng, et al., "Perceptual learning improves contrast sensitivity and visual acuity in adults with anisometropic amblyopia"; Vision Research 46 (2006); pp. 739-750.

Marcos, Susana, et al., "Influence of adaptive-optics ocular aberration correction on visual acuity at different luminances and contrast polarities"; Journal of Vision (2008) 8(13):1; ISSN 1534-7362, doi: 10.1167/8.13.1; pp. 1-12.

\* cited by examiner

US 8,020,991 B2

TWO-EYE ADAPTIVE OPTICAL VISUAL PERCEPTION TRAINING METHOD AND APPARATUS THEREOF

BACKGROUND OF THE INVENTION

1. Field of Invention

The present invention relates to a two-eye adaptive optical visual perception training method and a training apparatus capable of several functions including two-eye aberration correction, visual function measurement (including but not limited to a contrast threshold measurement and a two-eye stereoscopic acuity measurement), visual perception training (including but not limited to two-eye contrast sensitivity co-training and two-eye stereoscopic vision training). Finer visual stimulus is obtained by correcting aberrations of two eyes by means of an adaptive optical system, and then human eye acuity limit of two eyes can be measured, and thereby the visual perception training effect and visual function can be efficiently improved by performing visual perception training on two eyes with such apparatus.

2. Description of Prior Art

The development of vision of human is a progressive process. The eyeballs have grown to a certain extent when a person is born. However, the growing is not full in terms of anatomy or physiological function, and the eyeballs will continue growing in a long term thereafter. The normal development of Vision requires two conditions, one is the postnatal developing processing, and the other is external visual stimulus. Ages 0-7 are the golden stage for vision development, during which if the eyes are shaded for a long time, the vision will not develop and remain at a low level due to deficiency of normal visual stimulus from external images.

The function of the eyeballs is dominant for the vision of a person. Usually, an eyeball has no so perfect optical characteristic and whose capability is affected by various factors including, for example, diffraction of pupil, aberration from cornea and lens and dispersion of aqueous humor (R. Williams, D., & Hofer, H., Formation and Acquisition of the Retinal Image. In: J. S. W. Leo M. Chalupa (Ed.) The Visual Neurosciences, the MIT Press, Cambridge, Mass., London, England, 2003).

Generally, the effect due to the dispersion of aqueous humor is so small that is negligible. The aberration is large while the diffraction is small if the pupil becomes large, whereas the aberration is small while the diffraction is large if the pupil becomes small. The aberration of human eyes includes low-order aberration and high-order aberration, the former can be easily corrected but the latter is difficult to be corrected.

Recently, many researchers (Geun-Young Yoon and David R. Williams, Visual Performance after correcting the monochromatic and chromatic aberrations of the eye, J. Opt. Soc. Am. A/Vol. 19, No. 2) attempt to apply the Adaptive Optics technology in the research of vision to explore the relationship between the high-order aberration and normal vision and to explore the limit for spatial vision. However, it is not agreed whether a supernormal vision can be reached after all is the aberration (including the low order and the high order) of a visual system are corrected (Marcos, S., Sawides, L., Gambra, E., & Dorronsoro, C., Influence of adaptive-optics ocular aberration correction on visual acuity at different luminances and contrast polarities. 8: 1-12, 2008).

A visual system can only correctly develop with the aid of visual experiences (Chiu, C., & Weliky, M., The Role of Neural Activity in the Development of Orientation Selectivity. In: J. S. W. Leo M. Chalupa (Ed.) The Visual Neurosciences, The Mit Press, Cambrighe, Mass., London, England, 2003). The development of a fine acuity needs the fine development of the visual nervous system which depends on clarity degree of imaging on the retina for the optical system of an eyeball. An image cannot be clearly generated on the retina due to the high-order aberration and dispersion. The spatial cut off frequency that can be differentiated by the visual nervous system will be no larger than the highest spatial frequency of the image generated on the retina by the eyeballs.

The visual perception leaning process shows that the identification capability of the nervous system for a certain image will be largely improved via learning, which indicates that the nervous system is trainable even for an adult. Many psychological tests reveal that an adult can increase his success ratio and speed for a lot of visual perception tasks by learning (Zhou Y F, Huang C B, Xu P J, Tao L M, Qiu Z P, Li X R and Lu Z L, Perceptual Learning Improves Contrast Sensitivity and Visual Acuity in Adults with Anisometropic Amblyopia. Vision Research, 46(5): 739-750, 2006). However, the prior visual perception learning process uses eyeglass to correct the low-order aberration, and an image cannot be clearly generated on the retina due to the still existed high-order aberration and dispersion. Accordingly, the simple visual perception leaning process improves the visual function to an extent limited by the clarity of the image.

In view that the visual nervous system is trainable, the present invention combines the adaptive optical aberration correction technique and the visual perception learning technique. The quality of the image generated on the retina can be largely improved after the aberration is corrected through the adaptive optical technique. If the two-eye visual perception leaning process is conducted with such fine visual stimulus, the acuity of the visual nervous system can be enhanced, and thereby the visual perception training effect and visual function of human eyes can be efficiently improved.

SUMMARY OF THE INVENTION

In view of above disadvantages in the prior arts, the present invention proposes a two-eye adaptive optical visual perception training method and a training apparatus capable of several functions including two-eye aberration correction, visual function measurement (including but not limited to a contrast threshold measurement and a two-eye stereoscopic acuity measurement), visual perception training (including but not limited to two-eye contrast sensitivity co-training and two-eye stereoscopic vision training). Finer visual stimulus is obtained by correcting aberrations of two eyes by means of an adaptive optical system, and then eye acuity limit of two eyes can be measured, and the visual perception training effect and visual function can be efficiently improved by performing visual perception training on two eyes with such apparatus.

According to the first aspect of the present invention, there is proposed a two-eye adaptive optical visual perception training method, comprising the step of: a two-eye wave aberration measurement step for measuring wave aberrations of the left and right eyes of a person to be tested by using a near infrared reference light source, a wavefront corrector and a wavefront sensor; a two-eye wave aberration correction step for driving and controlling the wavefront corrector to correct the wave aberrations of the left and right eyes of the person to be tested based on the measured wave aberrations of the left and right eyes of the tested person; and a two-eye visual perception training step for displaying on a sighting target display sighting targets of different spatial frequencies and different contrasts after they have been subjected to processing in a video processing circuit, and presenting the sighting targets to the tested person via the driven and controlled wavefront corrector, to conduct a two-eye visual function measurement process and a visual perception training process.

Preferably, the two-eye visual function measurement process consists in a single/two eye contrast threshold measurement, where the difficulty of the stimulus is adjusted in real time in response to the reply from the tested person according to an adjustment method of psychophysics in such a manner that the contrast of the sighting target to be displayed next is decreased if the number of continuous replies from the tested person that are correct reaches a first predetermined value, and the contrast is increased if the number of continuous replies that are wrong reaches a second predetermined value. The correctness of the tested person during the whole measurement process maintains at a level though the adjustment and then a single/two eye contrast threshold of single/two eye(s) of the tested person is obtained. A single/two eye contrast sensitivity is obtained by reversing the obtained single/two eye contrast threshold.

More preferably, the two-eye visual perception training process comprises steps of: measuring a left eye contrast threshold and a right eye contrast threshold of the tested person respectively for gratings of different spatial frequencies; selecting a spatial frequency corresponding to a predetermined contrast threshold based on the difference of the left eye contrast threshold and the right eye contrast threshold under different spatial frequencies; and conducting the visual perception training process by using the grating with the selected spatial frequency.

Alternatively, the two-eye visual perception training process comprises steps of: selecting the spatial frequency measured after the preceding visual perception training process; and conducting the visual perception training process by using the grating with the selected spatial frequency.

Preferably, the two-eye visual function measurement process consists in a two-eye stereoscopic acuity measurement which obtains a psychophysical curve of the tested person by measuring the correctness of the tested person for different aberrations of two eyes using a constant stimulus method of psychophysics. More preferably, the two-eye visual perception training process consists in steps of selecting a two-eye aberration according to the measured psychophysical curve; and conducting the two-eye visual perception training process for a to predetermined period by using the selected two-eye aberration.

According to the second aspect of the present invention, there is proposed a two-eye adaptive optical visual perception training apparatus, comprising: left and right eye wave aberration measurement sub-systems including a near infrared reference light source, a wavefront corrector and a wavefront sensor, for measuring eye wave aberrations of the left and right eyes of a person to be tested; left and right eye wave aberration correction sub-systems including a control unit and said wavefront corrector, for driving and controlling the wavefront corrector to correct the wave aberrations of the left and right eyes of the person to be tested based on the measured wave aberrations of the left and right eyes of the tested person; and a two-eye visual perception training sub-system including a video processing circuit, a sighting target display and said wavefront corrector, for displaying on the sighting target display sighting targets of different spatial frequencies and different contrasts after they have been subjected to processing in the video processing circuit, and presenting the sighting targets to the tested person via the driven and controlled wavefront corrector, to conduct a two-eye visual function measurement process and a visual perception training process.

Preferably, the wavefront corrector is selected from a group consisted of a deformable reflective mirror, a liquid crystal wavefront corrector, a Micromachined membrane deformable mirror, a Microelectromechanical deformable mirror, a Bimorph deformable mirror, and a liquid deformable mirror.

Preferably, the wavefront sensor is selected from a group consisted of a microlens-array-based Hartmann wavefront sensor, a microprism-array-based Hartmann wavefront sensor, a Curvature wavefront sensor and a Pyramid wavefront sensor.

Preferably, the sighting target display is selected from a group consisted of a CRT display, a commercial display, a liquid crystal display, a plasma display, an electro-luminescent display, and an organic luminescent display.

Preferably, the video processing circuit combines the R channel and the B channel from the normal video output and obtains a grayscale of or higher than 14 bits.

Preferably, the left and right eye wave aberration correction sub-systems share one and the same control unit.

Compared to the prior art, the present invention proposes the concept of applying the adaptive optical technology in the two-eye visual perception training process for the first time. The apparatus according to the present invention is capable of several functions including eye aberration correction, visual function measurement (including but not limited to a contrast threshold measurement and a two-eye stereoscopic acuity measurement), visual perception training (including but not limited to two-eye contrast sensitivity co-training and two-eye stereoscopic vision training). Compared with the prior visual perception training process, the apparatus can obtain fine visual stimulus by correcting aberrations of two eyes by means of an adaptive optical system, and then eye acuity limit of two eyes can be measured, and thereby the two-eye visual perception training effect and the visual function measurement of human eyes can be efficiently improved by performing visual perception training on two eyes with such apparatus.

BRIEF DESCRIPTION OF THE DRAWINGS

The above and other objects, features and advantages of the present invention will be clearer from the following detailed description about the non-limited embodiments of the present invention taken in conjunction with the accompanied drawings, in which.

DETAILED DESCRIPTION OF PREFERRED EMBODIMENTS

Hereunder, the present invention will be described in accordance with the drawings. In the following description, some particular embodiments are used for the purpose of description only, which shall not be understood as any limitation to the present invention but the examples thereof. While it may blur the understanding of the present invention, the conventional structure or construction will be omitted.

Figure 1:
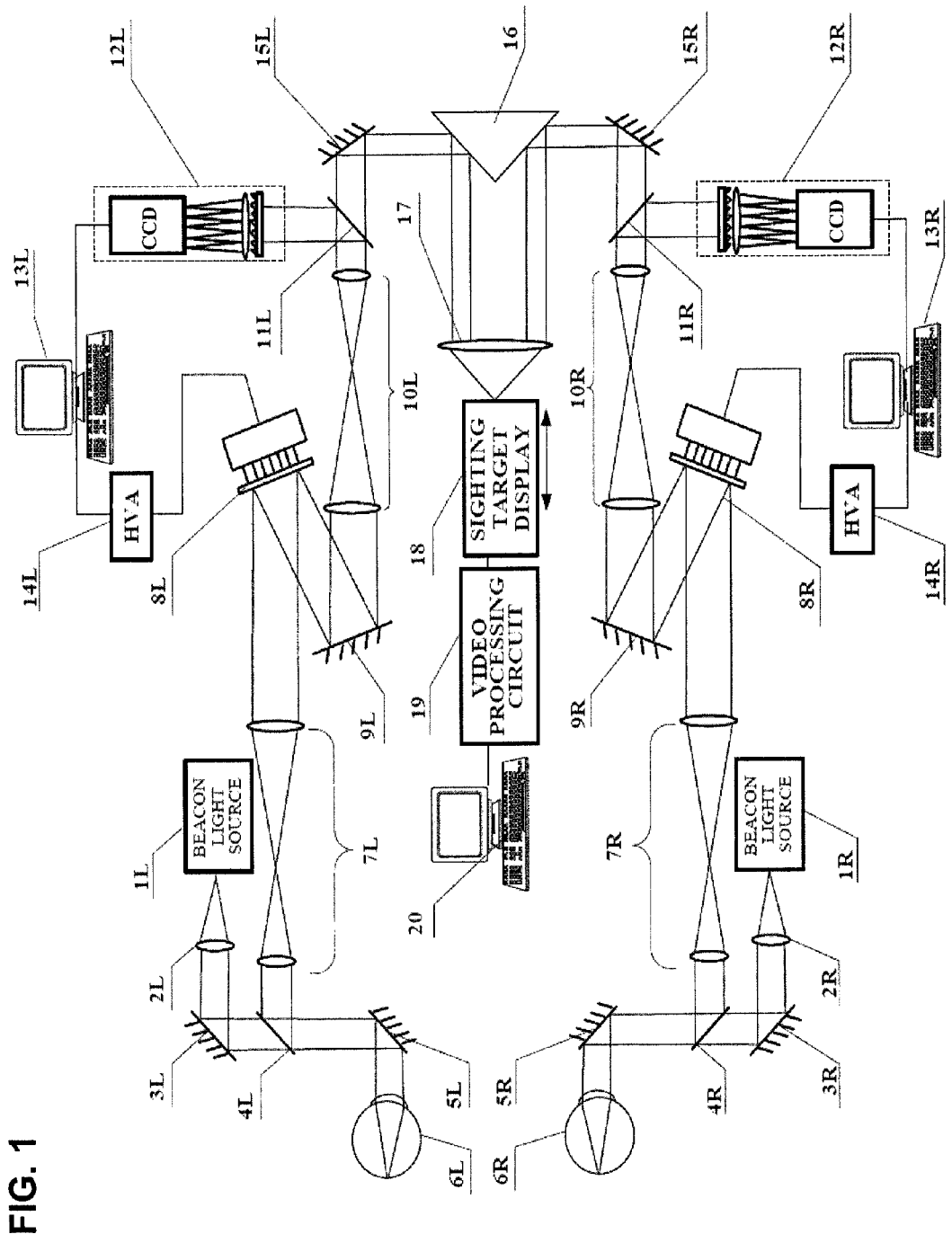
FIG. 1 is a schematic block diagram to show the respective units operating in the present invention.

FIG. 1 is a schematic block diagram to show the respective units operating in the present invention.

As shown in FIG. 1, the two-eye adaptive optical visual perception training apparatus according to the present invention comprises two sets of near infrared reference light sources 1L and 1R, two sets of collimating lenses 2L and 2R, two sets of first reflectors 3L and 3R, two sets of first beam splitters 4L and 4R, two sets of second reflectors 5L and 5R, two sets of beam matching afocal systems 7L and 7R, two sets of wavefront correctors 8L and 8R, two sets of third reflectors 9L and 9R, two sets of beam matching afocal systems 10L and 10R, two sets of splitters 11L and 11R, two sets of wavefront sensors 12L and 12R, computers 13L and 13R, two sets of high voltage amplifiers 14L and 14R, two sets of fourth reflectors 15L and 15R, a right angle prism 16, an imaging optical system 17, a sighting target display 18, a video processing circuit 19 and a computer 20. The left and right eyes of the person to be tested are denoted by the reference signs 6L and 6R, respectively. Additionally, though the computers 13L, 13R and 20 are shown as computers for different purposes in FIG. 1, it is obvious for those skilled in the art that the computers 13L, 13R and 20 may be one and the same computer or several computers physically separated from each other.

The two-eye adaptive optical visual perception training method according to the present invention comprises following three stages: a two-eye wave aberration measurement stage, a two-eye wave aberration correction stage and a visual perception training stage.

At the two-eye wave aberration measurement stage, the near infrared reference light sources 1L and 1R emit lights, which are collimated by the collimators 2L and 2R and reflected by the first reflectors 3L and 3R, the first beam splitters 4L and 4R and the second reflectors 5L and 5R, and finally enter into the pupil of the human eyes 6L and 6R. The lights are reflected from the eyeground of the eyes 6L and 6R, travel through the beam matching afocal systems 7L and 7R after reflection on the second reflectors 5L and 5R and the first beam splitters 4L and 4R, and reach the wavefront correctors 8L and 8R, which reflects the lights to the third reflectors 9L and 9R. The third reflectors 9L and 9R reflect the lights to the beam matching afocal systems 10L and 10R. The lights arrive at the wavefront sensors 12L and 12R after they travel through the beam matching afocal systems 10L and 10R and are subjected to reflection on the second beam splitters 11L and 11R. The wavefront sensors 12L and 12R transmit the measured error signal to the computers 13L and 13R to obtain the left eye wave aberration and the right eye wave aberration.

Then at the two-eye wave aberration correction stage, the computers 13L and 13R obtain the respective control voltages for the wavefront correctors 8L and 8R by running a computer control application based on the obtained left eye wave aberration and right eye wave aberration. The control voltages are amplified by the high voltage amplifiers 14L and 14R and applied on the wavefront correctors 8L and 8R to drive them, respectively, and thereby correcting the left eye wave aberration and the right eye wave aberration.

The visual perception training state starts after the two-eye wave aberration correction stage. A visual function measurement and vision training application executed on the computer 20 generates sighting targets of different spatial frequencies and different contrasts. The generated sighting targets are displayed on the sighting target display 18 after they are subjected to processing in the video processing circuit 19. The persons under test views the sighting targets displayed on the sighting target display 18 through the second reflectors 5L and 5R, the first beam splitters 4L and 4R, the beam matching afocal systems 7L and 7R, the wavefront correctors 8L and 8R, the third reflectors 9L and 9R, the beam matching afocal systems 10L and 10R, the second splitters 11L and 11R, the fourth reflectors 15L and 15R, the right angle prism 16 and the imaging lens 17. The two-eye visual perception training process and the human eye visual function measurement process (including but not limited to a contrast threshold measurement and a two-eye stereoscopic acuity measurement) commence.

The wavefront correctors 8L and 8R may be selected from a group consisted of a deformable reflective mirror, a liquid crystal wavefront corrector, a Micromachined membrane deformable mirror, a Microelectromechanical (MEMS) deformable mirror, a Bimorph deformable mirror and a liquid deformable mirror.

The wavefront sensors 12L and 12R may be selected from a group consisted of a microlens-array-based Hartmann wavefront sensor, a microprism-array-based Hartmann wavefront sensor (see the Chinese Invention Patent No. ZL03126431.X), a Curvature wavefront sensor and a Pyramid wavefront sensor. The sighting target display 18 may be selected from a group consisted of a CRT display, a commercial display, a liquid crystal display, a plasma display, an electro-luminescent display, and an organic luminescent display.

The video processing circuit 19 may combine the R channel and the B channel from the normal video output and obtains a grayscale of or higher than 14 bits (corresponding to 16384 levels), to meet the requirements for the human eye visual function measurement and the visual perception training. For example, the video processing circuit 19 may take the form of a circuit as disclosed in the Chinese Utility Patent No. ZL02220968.9.

Figure 2:
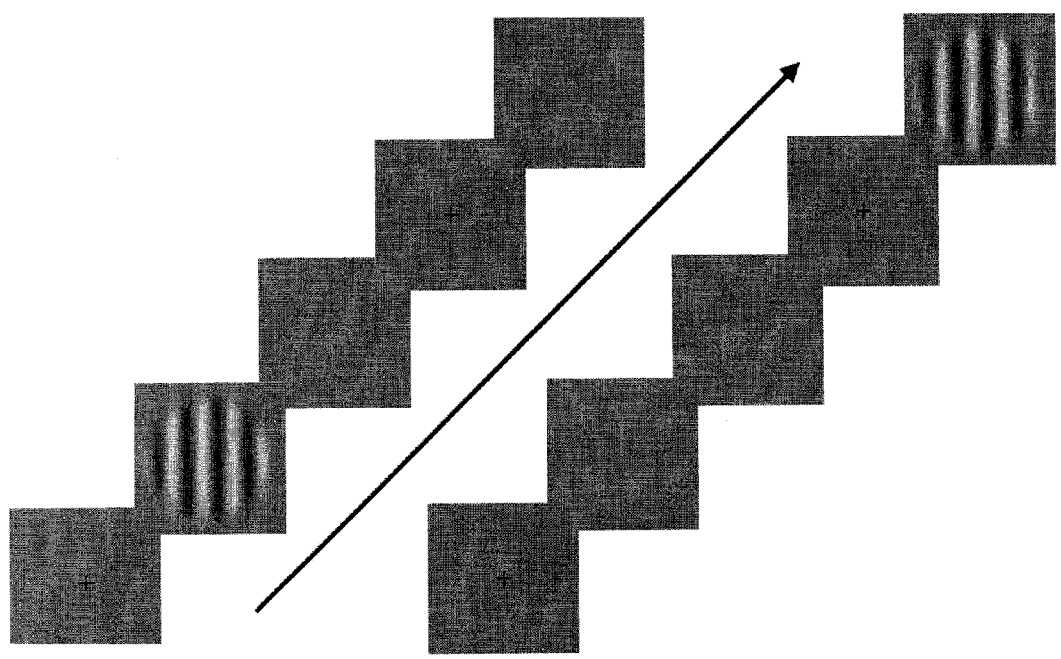
FIG. 2 is a schematic diagram to show the two-eye contrast sensitivity co-training process of the visual perception training apparatus according to the present invention. In the figures, respective units for the left and right eyes are denoted with suffixes "L" and "R" respectively so as to be differentiated.

FIG. 2 is a schematic diagram to show the two-eye contrast sensitivity co-training process of the visual perception training apparatus according to the present invention.

As shown in FIG. 2, during each training process, a crisscross appears on the screen two times sequentially, in company with an audio cue. Following each crisscross appearance, there may be presented a blank (a gray screen), or a target (i.e., a sinusoidal grating subjected to soft edge processing) to be detected. The person to be tested is required to press the left key to make a response when the grating appears after the crisscross occurs for the first time. The person is required to process the right key to make a response when the grating appears after the crisscross occurs for the second time. The process is repeated until all the training tasks, i.e., the tasks for the whole day, are completed.

In the present invention, the two-eye visual function measurement process consists in a human eye contrast threshold measurement, where the difficulty of the stimulus is adjusted in real time in response to the reply from the tested person according to the adjustment method of psychophysics in such a manner that the contrast of the sighting target to be displayed next is decreased, i.e., the difficulty is enhanced, if the tested person correctly responds continuously for three times, and the contrast of the sighting target to be displayed next is increased to lower the difficulty if the tested person wrongly responds. By such adjustment, the correctness of the tested person during the whole measurement process maintains nearly unchanged at a level. At the end, the contrast will converge to the human eye contrast threshold for the tested person. The human eye contrast sensitivity is obtained by reversing the human eye contrast threshold.

The two-eye contrast sensitivity co-training process measures contrast sensitivity curves of a single eye and two eyes of the tested person before and after the training process under eight spatial frequencies (including 0.6, 1, 2, 4, 8, 16, 24 and 32 cycles per degree) and the gratings of different spatial frequencies appear randomly. After the measurement, the contrasts of the eight spatial frequencies converge to the human eye contrast thresholds of the tested person. An appropriate spatial frequency (i.e., the cut off frequency of the poor eye) is selected for training based on the difference of the human eye contrast thresholds under different spatial frequencies. For example, the spatial frequency corresponding to a human eye contrast threshold of 0.4 of the poor eye of a person is deduced according to a contrast sensitivity curve of the poor eye obtained by measurement. During the training process, the frequency of the grating maintains unchanged, and the stimulus pattern for the left eye is the same as that for the right eye.

In the present invention, the two-eye visual function measurement process consists in a two-eye stereoscopic acuity measurement which obtains a psychophysical curve of the tested person by measuring the correctness of the tested person for different aberrations of two eyes using a constant stimulus method of psychophysics.

In the two-eye stereoscopic acuity measurement process, the correctness of the tested person for different two-eye aberrations is measured by using a constant stimulus method before and after the training, and thereby a stereoscopic vision psychophysical curve is obtained. An appropriate aberration is selected based on the psychophysical curve measured before the training, and the person is trained with the selected aberration for about 10 days.

The two-eye visual perception training process can adopt the conventional "test→training→re-test" method where the tested person is required to conduct the training tasks for a predetermined amount at the same time of each day under the selected spatial frequency (or selected aberration).

The two-eye contrast sensitivity co-training process can adopt the adjustment method similar as the contrast threshold measurement, and automatically takes the contrast threshold finally obtained after the training of the previous day as the initial value for the next day.

The two-eye stereoscopic vision training process can adopt the constant stimulus method similar as the two-eye stereoscopic acuity measurement. During the training process, the aberration for stimulus is fixed.

The foregoing description gives only the preferred embodiments of the present invention and is not intended to limit the present invention in any way. Thus, any modification, substitution, improvement or like made within the spirit and principle of the present invention should be encompassed by the scope of the present invention.

What is claimed is:

1. A two-eye adaptive optical visual perception training method, comprising the steps of:
a two-eye wave aberration measurement step for measuring wave aberrations of the left and right eyes of a person to be tested by using a near infrared reference light source, a wavefront corrector and a wavefront sensor;
a two-eye wave aberration correction step for driving and controlling the wavefront corrector to correct the wave aberrations of the left and right eyes of the person to be tested based on the measured wave aberrations of the left and right eyes of the tested person; and
a two-eye visual perception training step for displaying on a sighting target display sighting targets of different spatial frequencies and different contrasts after they have been subjected to processing in a video processing circuit, and presenting the sighting targets to the tested person via the driven and controlled wavefront corrector, to conduct a two-eye visual function measurement process and a visual perception training process,
wherein the video processing circuit combines the R channel and the B channel from a normal video output and obtains a grayscale of or higher than 14 bits.

2. The two-eye adaptive optical visual perception training method according to claim 1, wherein
the two-eye visual function measurement process consists in a single/two eye contrast threshold measurement, where the difficulty of the stimulus is adjusted in real time in response to the reply from the tested person according to an adjustment method of psychophysics in such a manner that the contrast of the sighting target to be displayed next is decreased if the number of continuous replies from the tested person that are correct reaches a first predetermined value, and the contrast is increased if the number of continuous replies that are wrong reaches a second predetermined value.

3. The two-eye adaptive optical visual perception training method according to claim 2, wherein
the correctness of the tested person during the whole measurement process maintains at a level though the adjustment and then a single/two eye contrast threshold of single/two eye(s) of the tested person is obtained, and thereby a single/two eye contrast sensitivity is obtained by reversing the single/two eye contrast threshold.

4. The two-eye adaptive optical visual perception training method according to claim 3, wherein the two-eye visual perception training process comprises steps of:
measuring a left eye contrast threshold and a right eye contrast threshold of the tested person respectively for gratings of different spatial frequencies;
selecting a spatial frequency corresponding to a predetermined contrast threshold based on the difference of the left eye contrast threshold and the right eye contrast threshold under different spatial frequencies; and
conducting the visual perception training process by using the grating with the selected spatial frequency.

5. The two-eye adaptive optical visual perception training method according to claim 3, wherein the two-eye visual perception training process comprises steps of:
selecting the spatial frequency measured after the preceding visual perception training process; and
conducting the visual perception training process by using the grating with the selected spatial frequency.

6. The two-eye adaptive optical visual perception training method according to claim 1, wherein the two-eye visual function measurement process consists in a two-eye stereoscopic acuity measurement which obtains a psychophysical curve of the tested person by measuring the correctness of the tested person for different aberrations of two eyes using a constant stimulus method of psychophysics.

7. The two-eye adaptive optical visual perception training method according to claim 6, wherein
the two-eye visual perception training process consists in steps of selecting a two-eye aberration according to the measured psychophysical curve; and
conducting the two-eye visual perception training process for a predetermined period by using the selected two-eye aberration.

8. A two-eye adaptive optical visual perception training apparatus, comprising:
left and right eye wave aberration measurement sub-systems including a near infrared reference light source, a wavefront corrector and a wavefront sensor, for measuring eye wave aberrations of the left and right eyes of a person to be tested;

left and right eye wave aberration correction sub-systems including a control unit and said wavefront corrector, for driving and controlling the wavefront corrector to correct the wave aberrations of the left and right eyes of the person to be tested based on the measured wave aberrations of the left and right eyes of the tested person; and a two-eye visual perception training sub-system including a video processing circuit, a sighting target display and said wavefront corrector, for displaying on the sighting target display sighting targets of different spatial frequencies and different contrasts after they have been subjected to processing in the video processing circuit, and presenting the sighting targets to the tested person via the driven and controlled wavefront corrector, to conduct a two-eye visual function measurement process and a visual perception training process, wherein the video processing circuit combines the R channel and the B channel from a normal video output and obtains a grayscale of or higher than 14 bits.

9. The two-eye adaptive optical visual perception training apparatus according to claim 8, wherein the wavefront corrector is selected from a group consisted of a deformable reflective mirror, a liquid crystal wavefront corrector, a Micromachined membrane deformable mirror, a Microelectromechanical deformable mirror, a Bimorph deformable mirror, and a liquid deformable mirror.

10. The two-eye adaptive optical visual perception training apparatus according to claim 8, wherein the wavefront sensor is selected from a group consisted of a microlens-array-based Hartmann wavefront sensor, a microprism-array-based Hartmann wavefront sensor, a Curvature wavefront sensor and a Pyramid wavefront sensor.

11. The two-eye adaptive optical visual perception training apparatus according to claim 8, wherein the sighting target display is selected from a group consisted of a CRT display, a commercial display, a liquid crystal display, a plasma display, an electro-luminescent display, and an organic luminescent display.

12. The two-eye adaptive optical visual perception training apparatus according to claim 8, wherein the left and right eye wave aberration correction sub-systems share one and the same control unit.

* * * * *